United States Patent
Gibson et al.

(10) Patent No.: US 8,889,174 B1
(45) Date of Patent: *Nov. 18, 2014

(54) ZERO-ORDER PROLONGED RELEASE COAXIAL IMPLANTS

(75) Inventors: John W. Gibson, Springville, AL (US);
Arthur J. Tipton, Homewood, AL (US);
Richard Holl, Ft. Collins, CO (US);
Stacey Meador, Vance, AL (US)

(73) Assignee: Durect Corporation, Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/589,847

(22) Filed: Aug. 20, 2012

Related U.S. Application Data

(63) Continuation of application No. 10/177,997, filed on Jun. 21, 2002, now Pat. No. 8,263,108.

(60) Provisional application No. 60/325,623, filed on Sep. 27, 2001, provisional application No. 60/300,404, filed on Jun. 22, 2001.

(51) Int. Cl.
*A61F 2/00* (2006.01)
*A61K 9/00* (2006.01)

(52) U.S. Cl.
CPC ................................ *A61K 9/0002* (2013.01)
USPC ........................................................ 424/426

(58) Field of Classification Search
None
See application file for complete search history.

(56) References Cited

U.S. PATENT DOCUMENTS

| | | | |
|---|---|---|---|
| 3,773,919 A | 11/1973 | Boswell | |
| 3,867,190 A | 2/1975 | Schmitt | |
| 3,887,699 A | 6/1975 | Yolles | |
| 4,010,125 A | 3/1977 | Schally | |
| 4,024,248 A | 5/1977 | Konig | |
| 4,293,539 A | 10/1981 | Ludwig | |
| 4,310,397 A | 1/1982 | Kaetsu | |
| 4,351,337 A * | 9/1982 | Sidman | 424/425 |
| 4,357,312 A | 11/1982 | Hsieh | |
| 4,450,150 A | 5/1984 | Sidman | |
| 4,526,938 A | 7/1985 | Churchill | |
| 4,591,496 A | 5/1986 | Cohen | |
| 4,652,441 A | 3/1987 | Okada | |
| 4,666,704 A | 5/1987 | Shalati | |

(Continued)

FOREIGN PATENT DOCUMENTS

| | | |
|---|---|---|
| EP | 0052510 | 5/1982 |
| EP | 0257560 | 8/1987 |

(Continued)

OTHER PUBLICATIONS

Anti-daibetic drugs. Wikipedia.com. Accessed online on Apr. 3, 2009 at http://en.wikipedia.org/wiki/Anti-diabetic drug.

(Continued)

*Primary Examiner* — Carlos Azpuru
*Assistant Examiner* — Casey Hagopian
(74) *Attorney, Agent, or Firm* — Pabst Patent Group LLP

(57) ABSTRACT

A coaxial implant has been developed using biodegradable polymeric materials. The coaxial implant has a core containing drug, surrounded by a semi-permeable membrane that controls the rate of release of material from the core. The core containing the drug and the polymer membrane(s) can be the same or different polymer. The core acts as a reservoir of drug, which partitions from the core polymer to form a saturated solution of drug at the polymer membrane.

17 Claims, 7 Drawing Sheets

(56) References Cited

U.S. PATENT DOCUMENTS

| | | |
|---|---|---|
| 4,675,189 A | 6/1987 | Kent |
| 4,677,191 A | 6/1987 | Tanaka |
| 4,720,384 A * | 1/1988 | Di Luccio et al. ............ 264/41 |
| 4,728,721 A | 3/1988 | Yamamoto |
| 4,745,160 A | 5/1988 | Churchill |
| 4,767,628 A | 8/1988 | Hutchinson |
| 4,849,228 A | 7/1989 | Yamamoto |
| 4,853,226 A | 8/1989 | Machida |
| 4,898,734 A | 2/1990 | Mathiowitz |
| 4,942,035 A | 7/1990 | Churchill |
| 4,962,091 A | 10/1990 | Eppstein |
| 4,981,696 A | 1/1991 | Loomis |
| 5,004,602 A | 4/1991 | Hutchinson |
| 5,039,660 A | 8/1991 | Leonard |
| 5,075,115 A | 12/1991 | Brine |
| 5,079,005 A | 1/1992 | Gupta |
| 5,100,669 A | 3/1992 | Hyon |
| 5,110,904 A | 5/1992 | Haviv |
| 5,126,147 A | 6/1992 | Silvestri |
| 5,134,122 A | 7/1992 | Orsolini |
| 5,183,662 A | 2/1993 | Morita |
| 5,192,741 A | 3/1993 | Orsolini |
| 5,225,205 A | 7/1993 | Orsolini |
| 5,248,700 A | 9/1993 | Lance |
| 5,330,767 A | 7/1994 | Yamamoto |
| 5,330,768 A | 7/1994 | Park |
| 5,340,584 A | 8/1994 | Spicer |
| 5,342,622 A | 8/1994 | Williams |
| 5,366,734 A | 11/1994 | Hutchinson |
| 5,397,572 A | 3/1995 | Coombes |
| 5,410,016 A | 4/1995 | Hubbell |
| 5,413,797 A | 5/1995 | Khan |
| 5,439,688 A | 8/1995 | Orsolini |
| 5,456,917 A | 10/1995 | Wise |
| 5,470,582 A | 11/1995 | Supersaxo |
| 5,476,663 A | 12/1995 | Okada |
| 5,480,656 A | 1/1996 | Okada |
| 5,480,868 A | 1/1996 | Kamei |
| 5,518,730 A | 5/1996 | Fuisz |
| 5,525,646 A | 6/1996 | Lundgren |
| 5,545,408 A | 8/1996 | Trigg |
| 5,550,173 A | 8/1996 | Hammond |
| 5,567,431 A | 10/1996 | Vert |
| 5,569,468 A | 10/1996 | Modi |
| 5,575,987 A | 11/1996 | Kamei |
| 5,607,686 A | 3/1997 | Totakura |
| 5,610,214 A | 3/1997 | Olson |
| 5,620,697 A | 4/1997 | Tormala |
| 5,626,877 A | 5/1997 | Amsden |
| 5,629,008 A | 5/1997 | Lee |
| 5,631,020 A | 5/1997 | Okada |
| 5,633,002 A | 5/1997 | Stricker |
| 5,641,501 A | 6/1997 | Cooper |
| 5,648,097 A | 7/1997 | Nuwayser |
| 5,651,990 A | 7/1997 | Takada |
| 5,665,394 A | 9/1997 | Igari |
| 5,668,111 A | 9/1997 | Kamei |
| 5,733,567 A | 3/1998 | Arola |
| 5,747,058 A | 5/1998 | Tipton |
| 5,780,435 A | 7/1998 | Garnick |
| 5,795,591 A * | 8/1998 | Lee et al. ............... 424/473 |
| 5,817,328 A | 10/1998 | Gresser |
| 5,843,901 A | 12/1998 | Roeske |
| 5,843,902 A | 12/1998 | Garnick |
| 5,851,547 A | 12/1998 | Fujioka |
| 5,854,382 A | 12/1998 | Loomis |
| 5,871,771 A | 2/1999 | Zierenberg |
| 5,889,110 A | 3/1999 | Hutchinson |
| 5,916,585 A | 6/1999 | Cook |
| 5,916,596 A | 6/1999 | Desai |
| 5,945,128 A | 8/1999 | Deghenghi |
| 5,968,895 A | 10/1999 | Gefter |
| 5,972,366 A | 10/1999 | Haynes |
| 5,981,474 A | 11/1999 | Manning |
| 6,036,976 A | 3/2000 | Takechi |
| 9,522,535 | 3/2000 | Johnson |
| 6,045,830 A | 4/2000 | Igari |
| 6,065,476 A | 5/2000 | Agrawal |
| 6,077,523 A | 6/2000 | Deghenghi |
| 6,083,916 A | 7/2000 | Nonomura |
| 6,113,941 A | 9/2000 | Takada |
| 6,117,455 A | 9/2000 | Takada |
| 6,120,789 A | 9/2000 | Dunn |
| 6,130,200 A | 10/2000 | Brodbeck |
| 6,153,586 A | 11/2000 | Garnick |
| 6,159,490 A | 12/2000 | Deghenghi |
| 6,180,608 B1 | 1/2001 | Gefter |
| 6,180,609 B1 | 1/2001 | Garnick |
| 6,193,994 B1 | 2/2001 | Lee |
| 6,197,350 B1 | 3/2001 | Yamagata |
| 6,206,920 B1 | 3/2001 | Eliaz |
| 6,211,153 B1 | 4/2001 | Garnick |
| 6,217,893 B1 | 4/2001 | Pellet |
| 6,245,346 B1 | 6/2001 | RothenWeinhold |
| 6,258,382 B1 | 7/2001 | Takaoka |
| 6,267,981 B1 | 7/2001 | Okamoto |
| 6,319,512 B1 | 11/2001 | RothenWeinhold |
| 6,322,805 B1 | 11/2001 | Kim |
| 6,328,990 B1 | 12/2001 | Ducheyne |
| 6,337,318 B1 | 1/2002 | Trigg |
| 6,338,859 B1 | 1/2002 | Leroux |
| 6,344,061 B1 | 2/2002 | Leitao |
| 6,344,209 B1 | 2/2002 | Saito |
| 6,384,017 B1 | 5/2002 | Garnick |
| 6,423,686 B1 | 7/2002 | Roeske |
| 6,528,093 B1 | 3/2003 | Kamei |
| 6,565,874 B1 | 5/2003 | Dunn |
| 6,620,422 B1 | 9/2003 | Maquin |
| 6,699,833 B1 | 3/2004 | Gefter |
| 6,777,386 B2 | 8/2004 | Trigg |
| 2001/0018072 A1 | 8/2001 | Unger |
| 2001/0026804 A1 | 10/2001 | Boutignon |
| 2002/0031553 A1 | 3/2002 | Moyano |
| 2002/0037309 A1 | 3/2002 | Jaworowicz |
| 2002/0039594 A1 | 4/2002 | Unger |
| 2002/0086829 A1 | 7/2002 | Gefter |
| 2002/0176841 A1 | 11/2002 | Barker |
| 2003/0040482 A1 | 2/2003 | Roeske |
| 2003/0133982 A1 | 7/2003 | Heimlich |
| 2003/0171296 A1 | 9/2003 | Gefter |
| 2004/0115236 A1 | 6/2004 | Chan |

FOREIGN PATENT DOCUMENTS

| | | |
|---|---|---|
| EP | 0258780 | 8/1987 |
| EP | 0302582 | 2/1989 |
| EP | 0481732 | 4/1992 |
| EP | 669128 A1 | 8/1995 |
| EP | 0794961 | 8/2002 |
| EP | 0704222 | 11/2002 |
| EP | 1137400 | 11/2003 |
| EP | 0858323 | 3/2004 |
| GB | 2209937 | 6/1989 |
| GB | 2234169 | 1/1991 |
| WO | 9211843 | 7/1992 |
| WO | 9640757 | 12/1996 |
| WO | 9715285 | 5/1997 |
| WO | 9715389 | 5/1997 |
| WO | 9722357 | 6/1997 |
| WO | 9809613 | 7/1997 |
| WO | 9741836 | 11/1997 |
| WO | 9825642 | 6/1998 |
| WO | 0054745 | 9/2000 |
| WO | 02022154 | 3/2002 |
| WO | 02074247 | 9/2002 |
| WO | 03022297 | 3/2003 |
| WO | 2004078160 | 9/2004 |

OTHER PUBLICATIONS

Coaxial. Merriam-Webster Online Dictionary. Accessed online on Jun. 14, 2007 at http://www.m-w.com/cgi-bin/dictionary.

(56) References Cited

OTHER PUBLICATIONS

Dunn, et al., "Fibrous Delivery Systems for Antimicrobial Agents" in Polymeric Materials in Meidcation (Gebelein, et al. eds.) Plenum Publishing Corporation, pp. 47-59 (1985).

Insulin. Wikipedia.com. Accessed online on Apr. 3, 2009 at http://en.wikipedia.org/wiki/Insulin.

Mazzei T., et al. Pharmacokinectics, Endocrine and Antitumour Effects of Leuprolide Depot (TAP-144-SR) in Advanced Prostatic Cancer: A Dose-Repsonse Evaluation. Drugs on Exptl Clin Res. XV(8)373-387 (1989).

Widmark. Observation of the Solubility of Insulin. Jul. 10, 1923. Institute of Medical Chemistry. pp. 1-3.

Zhang,et all., "A mechanistic study of anitibiotic release from biodegradable poly (d,l-lactide) cylinders" J. Controlled Release 31:129-144 (1994).

Cowsar, et al., "Biodegradable and Nonbiodegradable Delivery Systems", Long Action Comtraceptive Delivery Systems, Chapter 12:145-162, Eds Zatuchni, et al., (1984).

Dunn, et al., "Fibrous Polymers for the Delivery of Contraceptive Steroids to the Female Reproductive Tract", Controlled Release of Pestioidies and Pharmaceuticals, Springer USA, Ed. RL Dunn, DH Beck and R Lee,125-146 (1981).

Gibson, et al., "Development of a Fibrous IUD Delivery System for Estradiol/Progesterone", Intrauterine Contraception, Publisher Harper and Row, Philadephia, PA, Chapter 31:215-226 (1985).

European Office Action for EP Application EP 02 759 093.4 mailed Aug. 1, 2014.

* cited by examiner

_US 8,889,174 B1_

ZERO-ORDER PROLONGED RELEASE COAXIAL IMPLANTS

This application is a continuation of pending prior application U.S. Ser. No. 10/177,997, filed Jun. 21, 2002, entitled "Zero-Order Prolonged Release Coaxial Implants", by John W. Gibson, Richard Holl, Stacey Meador, and Arthur Tipton, which claims priority to U.S. Ser. No. 60/300,404, filed Jun. 22, 2001 and U.S. Ser. No. 60/325,623, filed Sep. 27, 2001, all of which are herein incorporated in their entirety by reference.

The U.S. government may have rights in this invention by virtue of National Institute of Neurological Disorders and Stroke grant No. 1R43NS39703-01.

BACKGROUND OF THE INVENTION

The present invention is generally in the field of prolonged release devices for delivery of pharmaceuticals where there is a critical need for uniform, zero-order release kinetics.

The field of drug delivery has developed over the last thirty years to the point where it is now possible to tailor delivery of the drugs with close precision, over prolonged periods of time, from weeks to months, following a single administration. Prolonged controlled release has been achieved using several different devices. Examples include mini-implantable pumps for a variety of drugs especially chemotherapeutics and highly potent neuroactive drugs, silicon tubing with release controlling pores in the ends for birth control agents, co-axial implants, transdermal patches and microencapsulated formulations. All have advantages and disadvantages. The mini-pump is extremely precise, but very expensive to manufacture. The mini-implantable pumps, silicon tubing and previously described co-axial implants all must be removed using an invasive procedure once the drug has been delivered. The microencapsulated formulations can be made using entirely biodegradable materials, but the release properties are not as controlled, and there can be an initial burst of drug. This is problematic for some drugs, which may have serious side effects if delivered in excess of the desired dosage, or which may be ineffective if not delivered in a sufficiently high dosage. Transdermal patches are only useful for the few drugs that will pass through the skin, and where precision of delivery is not mandatory.

Cancer is diagnosed in over one million Americans annually, and it is the cause of one in five deaths in the United States (approximately 1,400/day). Common progression of the disease often leads to chronic unrelieved pain. The use of narcotic analgesics including fentanyl and sufentanil are becoming more widely accepted as the treatment of choice. Because of the potential for developing tolerance as well as the toxic side effects, long-acting dosage forms that produce minimal initial burst are needed. As discussed above, several products including transdermal patches and implantable infusion systems are currently on the market. Transdermal patches can be used for outpatient treatment and have a duration of three days per dose. Intravenous infusion and intrathecal infusion deliver narcotics more consistently and can be used for longer periods of time. Currently approved infusion products generally use an externally-worn or implanted pump, are bulky, require surgical procedures to implant and to explant, and are very expensive systems. Duros® sufentanil, an osmotic pump designed for 100-day delivery of sufentanil, is currently undergoing clinical testing. This implant is much smaller and easier to administer, which provides advantages over the currently approved pumps, but requires removal at the end of the dosing period. This type of implant is described in WO 00/54745. A biodegradable implant could eliminate the need for removal thereby providing an added advantage to the patient, eliminating the cost and discomfort of the surgical explant procedure.

Implants that may be made of materials including biodegradable polymers have been described. For example, U.S. Pat. No. 4,666,704 to Shalati, et al., describes a controlled release implant, typically consisting of microparticle or pellets, that includes a core of a drug and water-insoluble drug and an outer polymeric membrane that can be formed by a coating of an organic solution of a water insoluble polymer and water soluble pore-forming agent. U.S. Patent application NO. 20020037309 to Jaworowicz, et al., describes an implant made of a polymer where the outer coating is annealed to decrease porosity and avoid burst release. Both of these require extensive processing steps, increasing cost, and may not be completely biodegradable.

It is therefore an object of the present invention to provide a controlled release device which is biodegradable, that releases over a prolonged period of time, and that provides very controlled zero-order release kinetics.

It is a further object of the present invention to provide a method of making such implants that is cost-effective, highly reproducible, and efficient.

SUMMARY OF THE INVENTION

A coaxial implant has been developed using entirely biodegradable polymeric materials. As referred to herein, a coaxial implant is a device having a core containing drug (which can be solid or liquid drug, or drug in a solid or liquid matrix), surrounded by a semi-permeable or microporous membrane that controls the rate of release of material from the core. As used herein, "semi-permeable" refers to device where drug dissolves into the membrane polymer and diffuses therethrough, and "microporous" refers to a device where the drug diffuses through pores in the membrane. The device can be formed by an extrusion process such as coaxial extrusion or it can formed by applying a coating to a preformed core that contains the active ingredient or filling the active-loaded core formulation into a preformed membrane material. In one embodiment, the polymer is processed to yield a semi-crystalline polymer, rather than an amorphous polymer. The core may contain the drug alone or mixed with another material such as a liquid carrier or biodegradable polymer. The core polymer, when used, and the polymer membrane(s) can be the same or different polymer. The polymer can be the same or different composition (i.e., both polyeaprolactone, or both poly(lactide-co-glycolide) of different monomer ratios, or polycaprolactone outside of a core of poly(lactide)), of the same or different molecular weights, and of the same or different chemical structure (i.e., crystalline, semi-crystalline or amorphous). In the case of a device with a dense polymer membrane, the core acts as a reservoir of drug, which partitions from the core polymer into the membrane polymer to form a saturated solution of drug at the interface between the core and membrane. Generally, a hydrophobic polymer is used with a hydrophobic drug and a hydrophilic polymer is used with more hydrophilic drugs. With very hydrophilic drugs, it may be preferable to use a microporous biodegradable polymer as the membrane polymer. In another embodiment, one of the core and the membrane is hydrophilic and the other is hydrophobic.

BRIEF DESCRIPTION OF THE DRAWINGS

FIG. 2a is of an implant having a 10 weight % naltrexone core, and ratio of the outer membrane radius to the inner membrane radius ($r_o:r_i$) of 1.1, 1.4, and 1.9. FIG. 2b is of an implant having a 30 weight % naltrexone core, with $r_o:r_i$ of 1.4, 1.6 and 1.9.

DETAILED DESCRIPTION OF THE INVENTION

I. Coaxial Implant Structure and Composition

Figure 1:
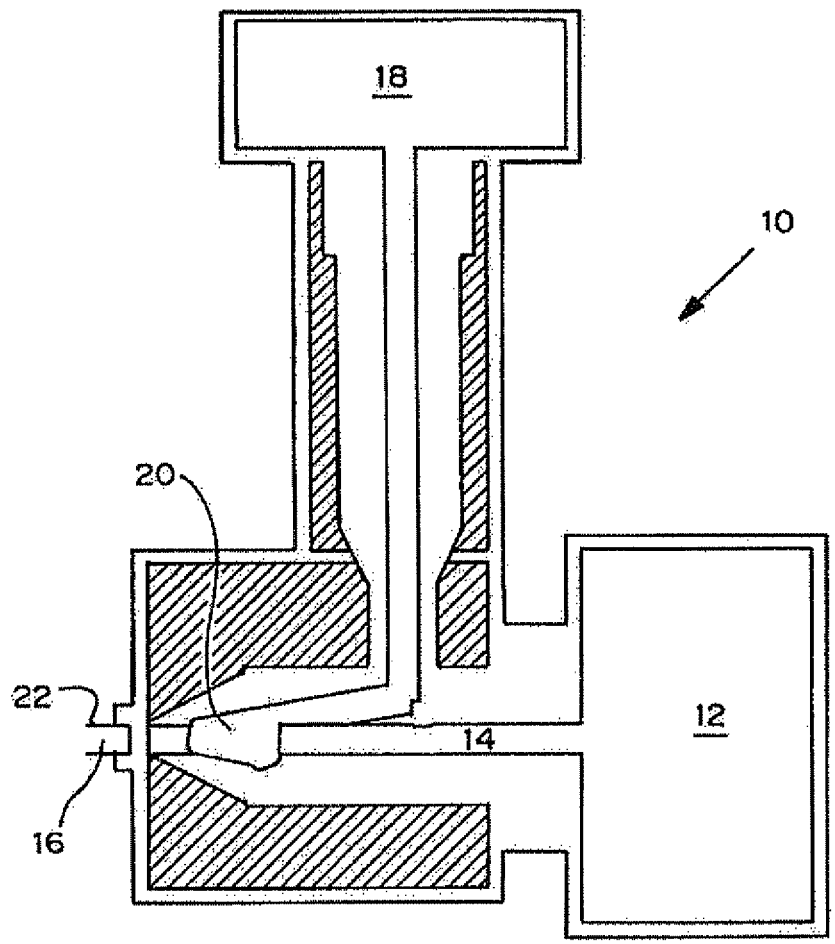
FIG. 1 is a schematic of the coaxial die to make the coaxial implant.

Methods for making fibrous implants for drug delivery are well known. See, for example, Cowsar and Dunn, Chapter 12 "Biodegradable and Nonbiodegradable Delivery Systems" pp. 145-162; Gibson, et al., Chapter 31 "Development of a Fibrous IUD Delivery System for Estradiol/Progesterone" pp. 215-226; Dunn, et al., "Fibrous Polymers for the Delivery of Contraceptive Steroids to the Female Reproductive Tract" pp. 125-146; Dunn, et al., "Fibrous Delivery Systems for Antimicrobial Agents" from Polymeric Materials in Medication ed. C. G. Gebelein and Carraher (Plenum Publishing Corporation, 1985) pp 47-59.

There are three common methods for producing fibers: wet spinning, dry spinning and melt spinning. Wet spinning involves extruding a solution of a polymer through an orifice into a nonsolvent to coagulate the polymer. In the dry-spinning process, a solution of a polymer is forced through an orifice and fed into a heated column that evaporates the solvent to form a filament. In melt-spinning, a thermoplastic polymer is heated above its melting point, extruded through an orifice, and cooled to form a filament. With coaxial spinning, the drug is extruded as the core of the fiber at the same time as the rate-controlling polymer membrane (also referred to as a "sheath"). A typical coaxial spinneret consists of two concentric rings. The drug, either in pure form or dispersed within a polymeric or nonpolymeric matrix, is pumped through the inner ring, where it forms the core. The rate-controlling polymer is pumped through the outer ring to form the sheath. As both streams of material emerge from the spinneret, they solidify to form the coaxial fiber or reservoir system. The rate at which the two materials are pumped to the coaxial spinneret determines the thickness of the sheath membrane and the size of the fiber.

The polymer or drug is liquified for extrusion either by melting or dissolution in a solvent. The preferred method of preparation of coaxial implants is melt extrusion in which two extruders are used to process the core formulation and the membrane material. The core formulation is fed to the center tube of a coaxial die and the membrane material is fed to a concentric outer ring of the same die such that the membrane material forms a uniform coating on the core as the materials exit the die. The relative diameters of the core and membrane are controlled by the dimensions of the die, the extrusion conditions, the relative extrusion rates of the two extruders, and the relative take-off speed. In this way, the core diameter and membrane thickness can be independently controlled.

Another method of preparing the coaxial implant is to first prepare a core formulation by a simple extrusion process and then form the membrane by a surface treatment of the monolithic core. The surface treatment may be accomplished by annealing the surface by exposure to elevated temperature or to a solvent for the polymer excipient so that the polymer forms a thin skin at the surface, which then functions as a rate controlling membrane. The membrane also may be added by applying a coating of the membrane formulation by a solution coating process. The solution coating process could be used to apply additional layers of different compositions thereby constructing multilayer coaxial implants.

Yet another method of preparing the coaxial implant is to first prepare the membrane as an empty tube, and then add the core formulation by injecting it into the center of the tube. As an example, the core formulation may consist of drug incorporated into a liquid matrix such as the non-polymeric, non-water soluble matrix described in U.S. Pat. No. 5,747,058 and U.S. patent application Ser. No. 09/385,107, the entire contents of both hereby incorporated by reference.

Although generally formed in a geometry where the cross-section is a circle, the implant can also be prepared with any other cross-sectional geometry, for example, an ellipsoid, a lobe, a square, or a triangle.

The drug can be added to the formulation in a variety of ways. If the core formulation contains a liquid carrier then the drug and carrier can be mixed to form a slurry. If the core formulation contains a polymer, the drug and polymer can be mixed by solvent-blending, dry blending, or melt blending. More uniform mixing may be obtained by extruding the drug-matrix twice. In the preferred embodiment, the core is formulated by dry blending the drug and polymer, melt extruding the blend, and grinding the extrudate to form a feedstock for the second extrusion. The drug loading in the core may be in the range of about 0.1 to 80 wt % when either liquid carriers or polymers are used in the core formulation and as high as 100% when only drug is used. A more preferred loading is in the range of about 10 to about 60 wt % and the most preferred loading is in the range of about 20 to about 50 wt %.

In any case, the final implant is formed by cutting the core/membrane formulation to the appropriate length for the desired dose and sealing the exposed ends of the core. For some applications, an initial loading dose may be desired, which can be accomplished for certain drugs by sealing only one or neither of the exposed ends so that there is a brief period of higher release. Several methods can be used to seal the ends of the implants. lithe implant contains a solid core it can be sealed by coating with a solution of the membrane polymer or by applying the molten membrane polymer, or simply by cutting the implant with a hot knife or wire such that it is heat sealed as the cut is made. It the implant contains a liquid core, the ends may be heat sealed, or they may be sealed by placing a polymer plug into the lumen of the membrane formulation. When a polymer plug is used, it may be optionally heat sealed to the membrane.

The coaxial implants may be prepared in a variety of sizes depending on the total dose of drug and the envisioned method of administration. In a preferred embodiment, the overall diameter is between 0.05 and 5.0 mm. For subcutaneous administration in humans, an overall diameter of between 1.0 and 4.0 mm may be more preferred. The length of the coaxial implant is typically between about 0.3 cm and 10 cm. For subcutaneous implantation, a more preferred length is between about 0.3 cm and 3.0 cm.

The membrane formulation is selected to provide the needed flux of drug (active agent) for an implant of given dimensions. For most practical applications, the membrane thickness will be within about 2% to about 40% of the overall implant diameter. It is preferred that the membrane thickness be between about 5% to about 30% of the total diameter. The membranes may be dense membranes with no porosity or they may be highly porous having pores of about 1 to about 30 microns and pore volumes of between about 5% and about 70%. The membrane may also contain the active ingredient at a lower loading than is contained in the core, or it may contain a different active ingredient than is contained in the core. Regardless of whether the membrane is a dense membrane or a porous membrane, the desired permeability properties of the material need not necessarily be achieved during the initial extrusion or coating step. Downstream processing means may be employed to achieve the final properties of the membrane. When semicrystalline polymers are used in the membrane, the crystallinity can be controlled by the cooling rate and conditions. The properties can also be altered by drawing the extruded formulation. Drawing is generally accomplished by passing the material around two or more sets of godets which are operated at progressively faster speeds as the material passes further down the line. The material may pass through heated ovens between the godets so that the temperature can be carefully controlled to further influence the crystallinity of the membrane. Drawing may also be used to control the final diameter of the material.

Because the coaxial structures are prepared by a continuous extrusion process, they can be any length that is convenient for handling. If the formulation is sufficiently flexible, it can be wound onto a spool or into a coil and held in this way prior to cutting. Alternatively, the material can be collected as shorter lengths of perhaps a few centimeters or meters and held prior to cutting. It is also possible to cut the material to the finished implant length as it is produced using a flywheel type of cutter that is situated just downstream of the coaxial die.

II. Process Materials

A. Polymer

The processes disclosed herein can be used to form coaxial implants from a variety of materials, preferably biocompatible and biodegradable polymers. Biodegradable, as defined herein, means the polymer will degrade or erode in vivo to form smaller chemical species, wherein the degradation can result, for example, from enzymatic, chemical, and physical processes. The term "biocompatible" is used herein to refer to a polymer and any degradation products of the polymer that are non-toxic to a recipient and present no significant, deleterious or untoward effects on the recipient's body. Examples of suitable biocompatible, biodegradable polymers include polyhydroxy acids, such as poly(lactide)s, poly(glycolide)s, poly(lactide-co-glycolide)s, poly(lactic acid)s, poly(glycolic acid)s, and poly(lactic acid-co-glycolic acid)s, polyanhydrides, polyorthoesters, polyetheresters, polyethylene glycol, polycaprolactone, polyesteramides, polyphosphazines, polycarbonates, polyamides, and copolymers and blends thereof. Preferred materials are polycaprolactone, poly(lactide)s, poly(glycolide)s, and copolymers thereof.

Representative natural polymer materials include polysaccharides and proteins.

B. Solvent

If the polymer and active agent are solvent blended, the selection of the solvent used in the process generally depends on the polymer and active agent chosen, as well as the particular means of solvent removal to be employed. Organic solvents, such as acetone, methyl ethyl ketone, tetrahydrofuran, ethyl lactate, ethyl acetate, dichloromethane, and ethyl acetate/alcohol blends, are preferred for use with PLGs and PCL.

C. Active Agent

Essentially any substance, or agent, can be incorporated using the processes described herein. The substance preferably is an active agent. As used herein, the term "active agent" refers to an agent which possesses therapeutic, prophylactic, or diagnostic properties in vivo, for example when administered to an animal, including mammals, such as humans. Examples of suitable therapeutic and/or prophylactic active agents include proteins, such as hormones, antigens, and growth factors; nucleic acids, such as antisense molecules; and smaller molecules, such as antibiotics, steroids, decongestants, neuroactive agents, anesthetics, sedatives, and antibodies, such as antibodies that bind to growth hormone receptors, including humanized antibodies, adjuvants, and combinations thereof. Examples of suitable diagnostic and/or therapeutic active agents include radioactive isotopes and radioopaque agents.

The active agent can include organic molecules such as a drug, peptide, protein, carbohydrate (including monosaccharides, oligosaccharides, and polysaccharides), nucleoprotein, mucoprotein, lipoprotein, synthetic polypeptide or protein, or a small molecule linked to a protein, glycoprotein, steroid, nucleic acid (any form of DNA, including cDNA, or RNA, or a fragment thereof), nucleotide, nucleoside, oligonucleotides (including antisense oligonucleotides), gene, lipid, hormone, vitamin, including vitamin C and vitamin E, or combination thereof.

Representative therapeutic active agents include immunosuppressants, antioxidants, anesthetics, chemotherapeutic agents, steroids (including retinoids), hormones, antibiotics, antivirals, antifungals, antiproliferatives, antihistamines, anticoagulants, antiphotoaging agents, melanotropic peptides, nonsteroidal and steroidal anti-inflammatory compounds, antipsychotics, and radiation absorbers, including UV-absorbers. Other non-limiting examples of active agents include anti-infectives such as nitrofurazone, sodium propionate, antibiotics, including penicillin, tetracycline, oxytetracycline, chlorotetracycline, bacitracin, nystatin, streptomycin, neomycin, polymyxin, gramicidin, chloramphenicol, erythromycin, and azithromycin; sulfonamides, including sulfacetamide, sulfamethizole, sulfamethazine, sulfadiazine, sulfamerazine, and sulfisoxazole, and anti-virals including idoxuridine; antiallergenics such as antazoline, methapyritene, chlorpheniramine, pyrilamine prophenpyridamine, hydrocortisone, cortisone, hydrocortisone acetate, dexamethasone, dexamethasone 21-phosphate, fluocinolone, triamcinolone, medrysone, prednisolone, prednisolone 21-sodium succinate, and prednisolone acetate; desensitizing agents such as ragweed pollen antigens, hay fever pollen antigens, dust antigen and milk antigen; decongestants such as phenylephrine, naphazoline, and tetrahydrazoline; miotics and anticholinesterases such as pilocarpine, esperine salicylate, carbachol, diisopropyl fluorophosphate, phospholine iodide, and demecarium bromide; parasympatholytics such as atropine sulfate, cyclopentolate, homatropine, scopolamine, tropicamide, eucatropine, and hydroxyamphetamine; sympathomimetics such as epinephrine; sedatives and hypnotics such as pentobarbital sodium, phenobarbital, secobarbital sodium, codeine, (a-bromoisovaleryl)urea, carbromal; psychic energizers such as 3-(2-aminopropyl)indole acetate and 3-(2-aminobutyl)indole acetate; tranquilizers such as reserpine, chlorpromayline, and thiopropazate; androgenic steroids such as methyl-testosterone and fluorymesterone; estrogens such as estrone, 17-β-estradiol, ethinyl estradiol, and diethyl stilbestrol; progestational agents such as progesterone, megestrol, melengestrol, chlormadinone, ethisterone, norethynodrel, 19-norprogesterone, norethindrone, medroxyprogesterone and 17-β-hydroxy-progesterone; humoral agents such as the prostaglandins, for example $PGE_1$, $PGE_2$ and $PGF_2$; antipyretics such as aspirin, sodium salicylate, and salicylamide; antispasmodics such as atropine, methantheline, papaverine, and methscopolamine bromide; antimalarials such as the 4-aminoquinolines, 8-aminoquinolines, chloroquine, and pyrimethamine, antihistamines such as diphenhydramine, dimenhydrinate, tripelennamine, perphenazine, and chlorphenazine; cardioactive agents such as dibenzhydroflume thiazide, flumethiazide, chlorothiazide, and aminotrate, natural and synthetic bioactive peptides and proteins, including growth factors, cell adhesion factors, cytokines, and biological response modifiers.

In one embodiment, the incorporated material is a vaccine and the substance to be delivered is an antigen. The antigen can be derived from a cell, bacteria, or virus particle, or portion thereof. As defined herein, antigen may be a protein, peptide, polysaccharide, glycoprotein, glycolipid, nucleic acid, or combination thereof, which elicits an immunogenic response in an animal, for example, a mammal, bird, or fish. The immunogenic response can be humoral or cell-mediated. In the event the material to which the immunogenic response is to be directed is poorly antigenic, it may be conjugated to a carrier, such as albumin, or to a hapten, using standard covalent binding techniques, for example, with one of the several commercially available reagent kits. Examples of preferred antigens include viral proteins such as influenza proteins, human immunodeficiency virus (HIV) proteins, and hepatitis A, B, or C proteins, and bacterial proteins, lipopolysaccharides such as gram negative bacterial cell walls and *Neisseria gonorrhea* proteins, and parvovirus.

In the preferred embodiment, the substance to be delivered is a drug such as a narcotic analgesic, which is very potent, and where the dosage must be narrowly maintained within the safe and effective levels. Examples include sufentanil and fentanyl. Naltrexone and other narcotic antagonists are also preferred active agents as are interferon, cromolyn sodium and leuprolide acetate or other LHRH agonists or antagonists.

The amount of active agent to be incorporated and the amount used in the process will vary depending upon the particular active agent, the desired effect of the active agent at the planned release levels, and the time span over which the agent should be released. The process can be used to incorporate more than one active agent. The active agent also can be mixed with one or more excipients, such as stabilizing agents, known in the art.

D. Excipients and Pore Forming Agents

Suitable materials that can be added to the membrane polymer to achieve the desired porosity include sucrose, dextrose, sodium chloride, sorbitol, lactose, polyethylene glycol, mannitol, fructose, polyvinyl pyrrolidone or appropriate combinations thereof. These materials can also be mixed with or incorporated into the core to provide bulking, alter release rates, increase water uptake, control pH, provide structural support, and other uses known to those skilled in the art.

III. Methods of Use

The coaxial implants are implanted using minimally invasive procedures at a site where release is desired. These can be implanted using trocars or catheters subcutaneously, intraperitoneally, intramuscularly, and intralumenally (intravaginally, intrauterine, rectal, periodontal).

The coaxial implants can be fabricated as part of a matrix, graft, prosthetic or coating, for example, intravascularly. Preferred actives for use in the treatment of restenosis include heparin and taxol. These implants can also be used in release of drug near the nerve plexus, or below the bladder, near the pelvic nerve plexus.

The coaxial implant is designed so that the drug is released in the desired dosage over a defined period of time. The coaxial implant is designed so that it degrades after release is achieved.

The present invention will be further understood by reference to the following non-limiting examples.

Example 1

Biodegradable Coaxial Implants for Delivery of Narcotic Analgesics

Coaxial extrusion has been evaluated as an efficient process for producing implants capable of delivering drugs at near zero-order rates. In this study the biodegradable polymer, poly (ε-caprolactone) (PCL) was evaluated in implants designed to deliver drug for 30 days. The study was undertaken to determine the feasibility of developing a fully biodegradable reservoir-type implant capable of delivering fentanyl or sufentanil for 30 days.

Experimental Methods

Materials

Naltrexone base (NTX), fentanyl base, and sufentanil base were obtained from Mallinckrodt, St. Louis, Mo. Poly (ε-caprolactone) (PCL) having an inherent viscosity of 1.31 dL/g in chloroform at 30° C. and 75:25 poly (DL-lactide-co-glycolide-co-, -caprolactone) (DL-PLCL) having an inherent viscosity of 0.65 dL/g were obtained from Birmingham Polymers, Inc., Birmingham, Ala.

Formulation Preparation

All formulations were prepared by a melt-extrusion process using two Randcastle Microtruders and a coaxial die. The active (NTX, fentanyl base, or sufentanil base) and PCL were solvent blended using dichloromethane. After most of the solvent had been evaporated, the mixtures were vacuum dried and ground through a 1-mm screen using a Retsch Ultracentrifugal Mill. The ground material was further dried under vacuum for at least 24 hours. Blends containing either 10 or 30 wt % active were prepared.

Coaxial rods containing NTX or fentanyl base were prepared by operating the two extruders simultaneously. FIG. 1 shows a schematic of the coaxial die 10 used during the extrusion. The active/PCL blends were processed via the first extruder 12 and fed through the center orifice 14 of the die 10 to form the implant core 10. Pure PCL was processed via the second extruder 18 and fed to the outer, concentric ring 20 of the coaxial die 10 to form the membrane 22. The resulting coaxial rod thus consists of an active/PCL core 16 and a PCL rate-controlling membrane 22. The relative thickness of the membrane is controlled by adjusting the extrusion rate of the second extruder relative to that of the first. After extrusion, individual implants with a diameter of approximately 1.5 mm were cut to a length of 2.0 cm. The exposed ends were than sealed by coating the ends with a solution of PCL in dichloromethane.

Coaxial rods containing sufentanil base were prepared by extruding monolithic rods containing sufentanil/polymer blends and cutting the rods to a length giving the desired amount of sufentanil. The rods were coated by dipping into a solution of polymer dissolved in dichloromethane. Individual coatings were applied until the desired membrane thickness was achieved.

Naltrexone Content Assay

The active content of individual naltrexone implants was determined by dissolving the implant in ethyl acetate, diluting the solution with HPLC mobile phase, and analyzing the resulting extract by HPLC.

In Vitro Dissolution

Active release was determined in vitro using a simple dissolution test. Individual naltrexone or fentanyl implants were placed in 2-oz. amber jars with 10 mL of buffer (phosphate buffered saline, pH 7.4, with 0.05% sodium azide) and incubated at 37° C. Periodically, a known volume of buffer was removed and replaced with fresh buffer. The drug concentration in each sample of buffer was determined by HPLC.

Individual sufentanil implants were placed in 8-oz amber jars containing 20 mL of buffer. After one hour, the total amount of buffer was increased to 70 mL. At each sampling time, a 10-mL aliquot of buffer was removed and replaced with 10 mL of fresh buffer. The concentration of sufentanil in each sample was determined by HPLC.

Results and Discussion

Several experiments were conducted to determine the optimal conditions for the coaxial extrusion. Table 1 shows the process conditions used during the NTX coaxial extrusion for the two Randcastle Extruders.

TABLE 1

Coaxial Extrusion Conditions

| Extrude Conditions | Core Extruder | Membrane Extruder |
|---|---|---|
| Zone 1 | 154° F. | 150° F. |
| Zone 2 | 170° F. | 158° F. |
| Zone 3 | 170° F. | 163° F. |
| Die Block | 168° F. | 165° F. |
| Die Block | 168° F. | 165° F. |
| Coaxial Die | 170° F. | 170° F. |

Figure 2A:
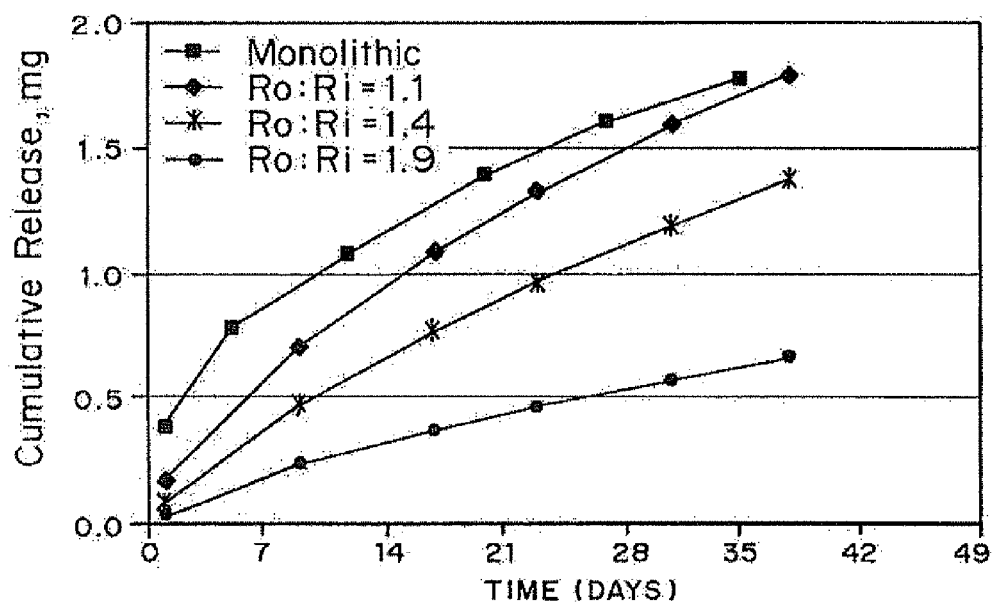
FIGS. 2a and 2b are graphs of the effect of various membrane thicknesses on the release of naltrexone base from coaxial implants, cumulative release (mg) versus time (days).
Figure 2B:
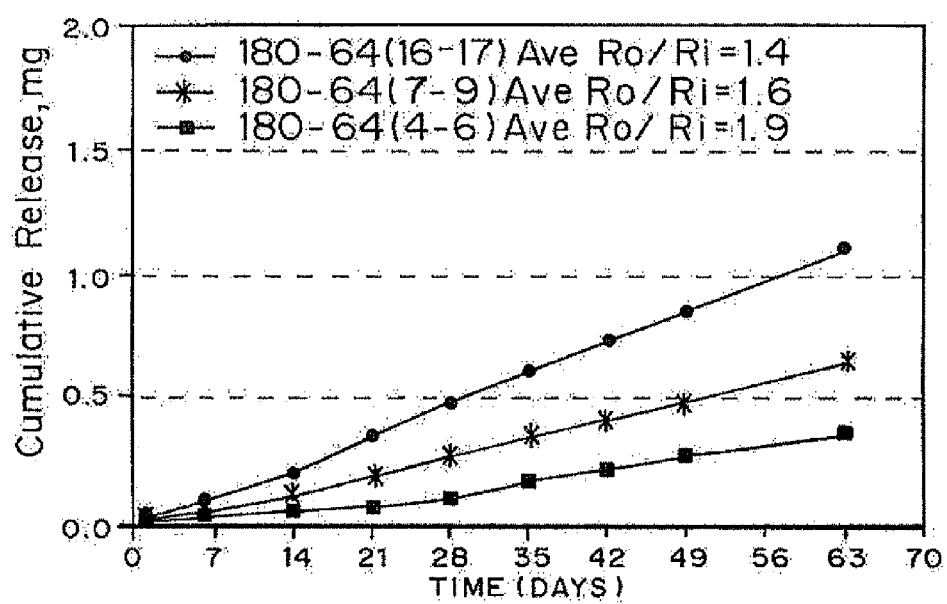

FIG. 2 shows the release of naltrexone base in mg/day for various implant formulations including the monolithic core and coated rods having different membrane thicknesses. The core and membrane thicknesses were determined by measuring the inner ($r_i$) and outer ($r_o$) radii of the implant. As expected, the membrane controls the rate of release of NTX base from the implant. The thicker the polymer membrane, the slower the release of naltrexone base from the coaxial implant.

Figure 3:
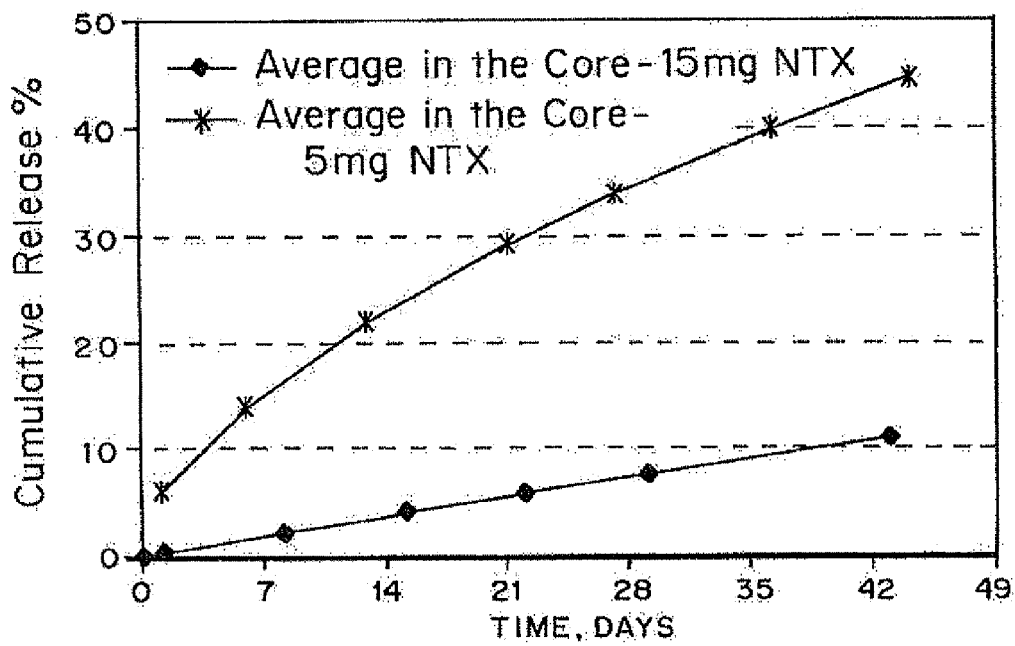
FIG. 3 is a graph of the effect of core loading (5 and 15 mg) on release of naltrexone from coaxial polycaprolactone ("PCL") implants, cumulative release (percentage) versus time (days).

FIG. 3 shows a comparison between core loadings for implants having a $r_o$:$r_i$ of 1.1. The lower loaded implants show a gradual decline in the rate of NTX release. This declining rate is due in part, to the low initial concentration of drug relative to the saturation solubility of drug in the core polymer. As drug is released and the concentration of active in the core falls below saturation, a zero-order release profile is not maintained. At the highest core loading, however, saturation and a zero-order release profile can be maintained for a longer duration.

Figure 4:
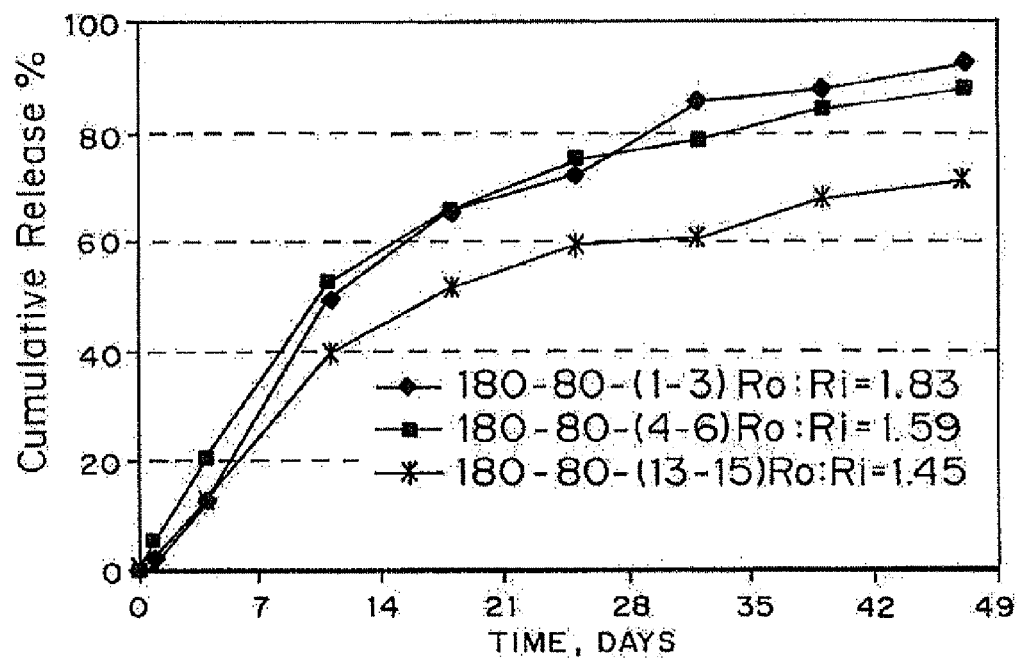
FIG. 4 is a graph of the effect of membrane thickness on the release of fentanyl from coaxial PCL implants, cumulative release (mg) versus time (days), for $r_o:r_i$ of 1.27, 1.45, 1.59, and 1.83, respectively.

FIG. 4 shows the release of fentanyl base from coaxial implants containing 10 wt % fentanyl base in the core. As with the NTX implants, the release of fentanyl becomes first order as the concentration in the core falls below saturation.

Figure 5:
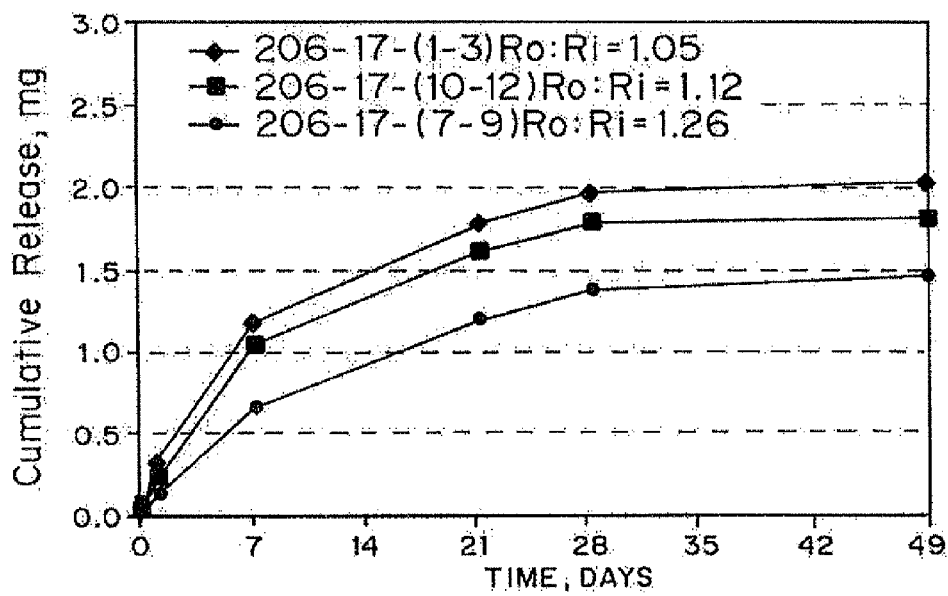
FIG. 5 shows the release of sufentanil base from coaxial implants containing 10 wt % sufentanil base in the core.
Figure 6:
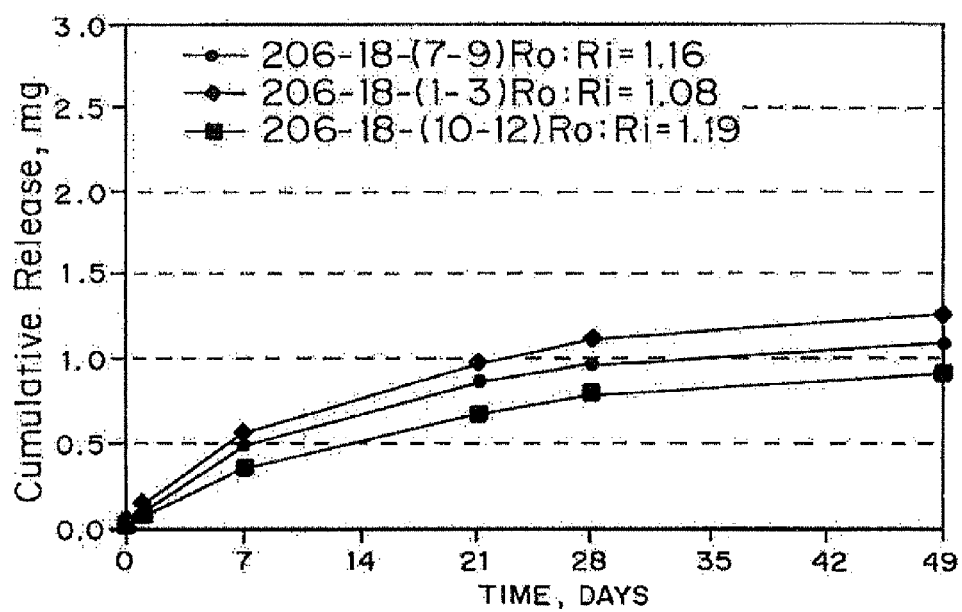
FIG. 6 shows the release of sufentanil base from coaxial implants containing 30 wt % sufentanil base in the core.

FIGS. 5 and 6 show the release of sufentanil base from coaxial implants containing, respectively, 10 and 30 wt % sufentanil base in the core.

Example 2

Biodegradable Coaxial Implants for Delivery of Cromolyn Sodium with Sodium Chloride as a Pore-Forming Agent in the Membrane The core material (50:50 wt/wt cromolyn sodium (cromolyn) and PCL with an inherent viscosity of 0.67 dL/g in chloroform at 30° C.) was blended together, compounded, and ground through a 1-mm screen using a Retsch Ultracentrifugal Mill. The membrane material (30% vol/vol sodium chloride (NaCl) and PCL with an inherent viscosity of 1.37 dL/g in chloroform at 30° C.) was blended, compounded, and ground the same as the core material. The core and membrane material were dried under vacuum for a minimum of 16 hours Coaxial rods were produced by operating the two Randcastle extruders simultaneously. The core material (cromolyn/PCL) was fed through the center orifice of the die on the first extruder to form the implant core. The membrane material (NaCl/PCL) was fed through the second extruder through the outer ring of the coaxial die to form the membrane. Individual implants with a diameter of approximately 2 mm were cut to a length of 2 cm. The exposed ends were sealed with the same polymer as the membrane.

Cromolyn release was determined in vitro using a simple dissolution test. Individual implants were placed in 4-oz amber jars with 40 mL of buffer (phosphate buffered saline, pH 7.4, with 0.05% sodium azide) and incubated at 37° C. Periodically, aliquots of buffer were removed and replaced with fresh buffer. The cromolyn concentration in each sample was determined by HPLC.

Figure 7:
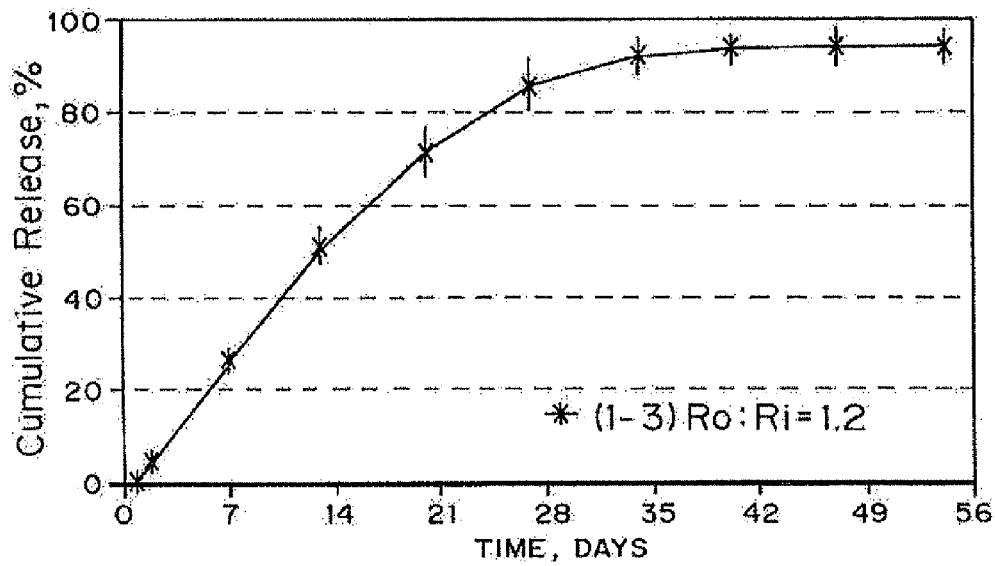
FIG. 7 shows the release of cromolyn sodium from coaxial implants containing 30 vol. % sodium chloride (pore forming agents)/PCL membrane and 50 wt % cromolyn sodium/PCL core. $r_o:r_i$=1.2.

FIG. 7 shows the release of cromolyn from coaxial implants with NaCl being used as the pore-forming agent.

Example 3

Biodegradable Coaxial Implants for Delivery of Cromolyn Sodium with Cromolyn Sodium as a Pore-Forming Agent in the Membrane The core material (50:50 wt/wt cromolyn sodium (cromolyn) milled and compounded with PCL with an inherent viscosity of 0.67 dL/g in chloroform at 30° C.) and the membrane material (30% vol/vol cromolyn milled and compounded with PCL with an inherent viscosity of 1.37 dL/g in chloroform at 30° C.) were processed and analyzed the same as in Example 2.

Figure 8:
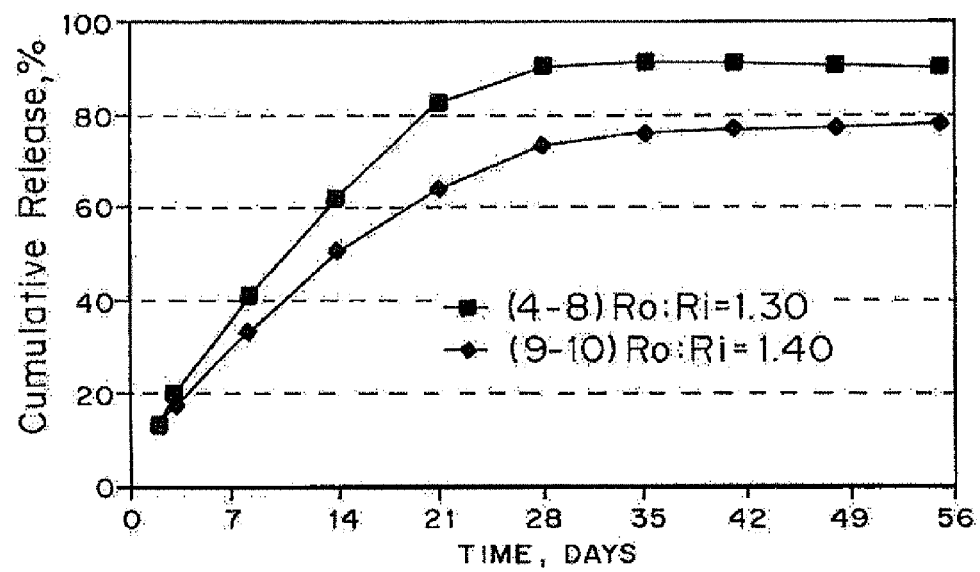
FIG. 8 shows the release of cromolyn sodium from coaxial implants containing 30 vol. % sodium chloride (pore forming agents)/PCL membrane and 50 wt % cromolyn sodium/PCL core. $r_o:r_i$=1.30 and 1.40.

FIG. 8 shows the release of cromolyn from coaxial implants with cromolyn being used as a pore-forming agent. As expected, the membrane controls the rate at which cromolyn is released. A thicker polymer membrane causes slower release of cromolyn.

Example 4

Biodegradable Coaxial Implants for Delivery of Cromolyn Sodium with Lactose as a Pore-Forming Agent in the Membrane The core material (50:50 wt/wt cromolyn sodium (cromolyn) milled and compounded with PCL with an inherent viscosity of 0.67 dL/g in chloroform at 30° C.) and the membrane material (30% vol/vol lactose milled and compounded with PCL with an inherent viscosity of 1.37 dL/g in chloroform at 30° C.) were processed and analyzed the same as in Example 2.

Figure 9:
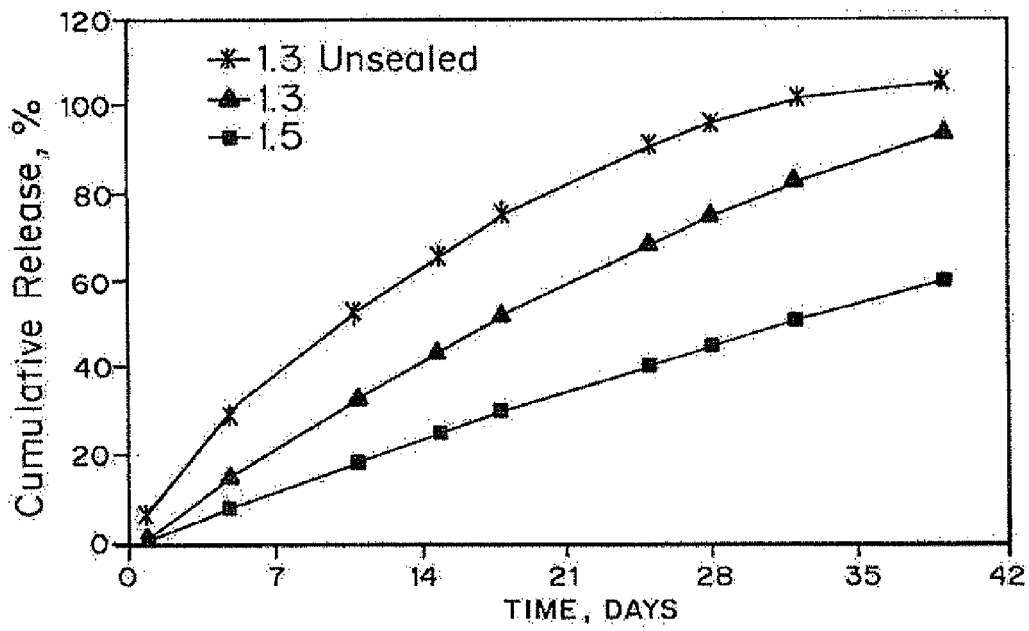
FIG. 9 compares the cumulative release (mg) of cromolyn sodium from sealed and unsealed coaxial implants containing 50 wt % cromolyn/PCL core with a 30 vol % lactose/PCL membrane. $r_o:r_i$=1.30 and 1.50.

FIG. 9 shows the release of cromolyn from coaxial implants. The graph compares the release from a sealed implant to the release of an unsealed implant. As expected, the unsealed implant releases faster than the sealed.

Example 5

Biodegradable Coaxial Implants for Delivery of Cromolyn Sodium from a Dense PEG 3K/90:10 DL-PLG Polymer Membrane The core material (50:50 wt/wt cromolyn sodium (cromolyn) milled and compounded with PCL with an inherent viscosity of 0.67 dL/g in chloroform at 30° C.) and the membrane material (PEG 3K/90:10 DL-PLG with an inherent viscosity of 0.89 dL/g in chloroform at 30° C.) were processed and analyzed the same as in Example 2.

Figure 10:
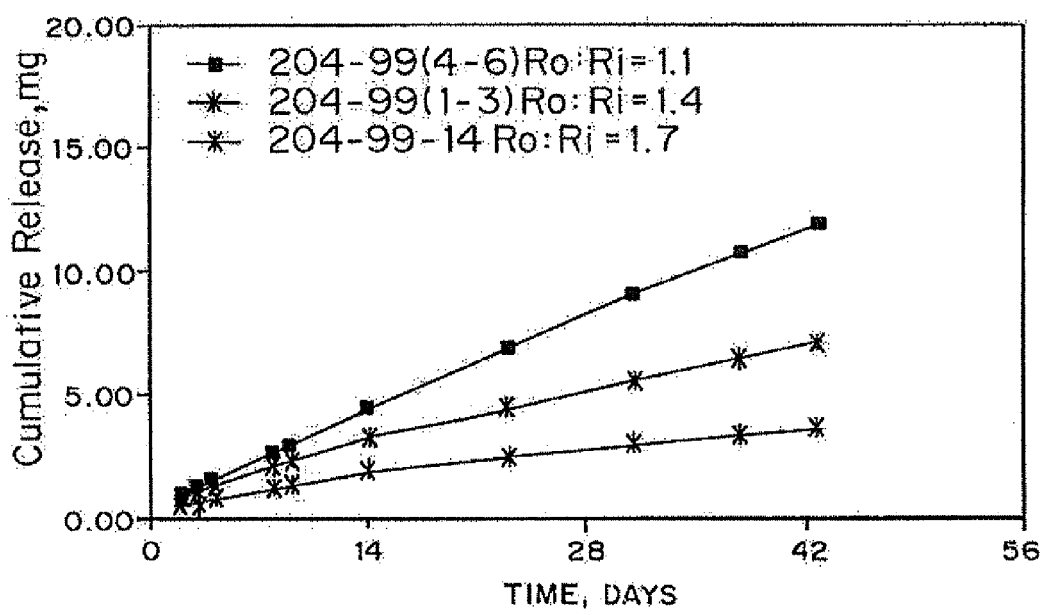
FIG. 10 shows the cumulative release of cromolyn sodium (mg) from coaxial implants containing 50 wt % cromolyn/PCL core with a dense hydrophilic polymer membrane, polyethylene glycol 3000/90:10 DL-polyethylene glycol membrane. $r_o:r_i$=1.1, 1.4 and 1.7.

FIG. 10 shows the release of cromolyn from coaxial implants with a dense hydrophilic polymer membrane.

Example 6

Biodegradable Coaxial Implants for Delivery of Cromolyn Sodium from a Dense PCL Membrane The core material (50:50 wt/wt cromolyn sodium (cromolyn) milled and compounded with PCL with an inherent viscosity of 0.67 dL/g in chloroform at 30° C.) and the membrane material (PCL with an inherent viscosity of 1.37 dL/g in chloroform at 30° C.) were processed and analyzed the same as in Example 2.

Figure 11:
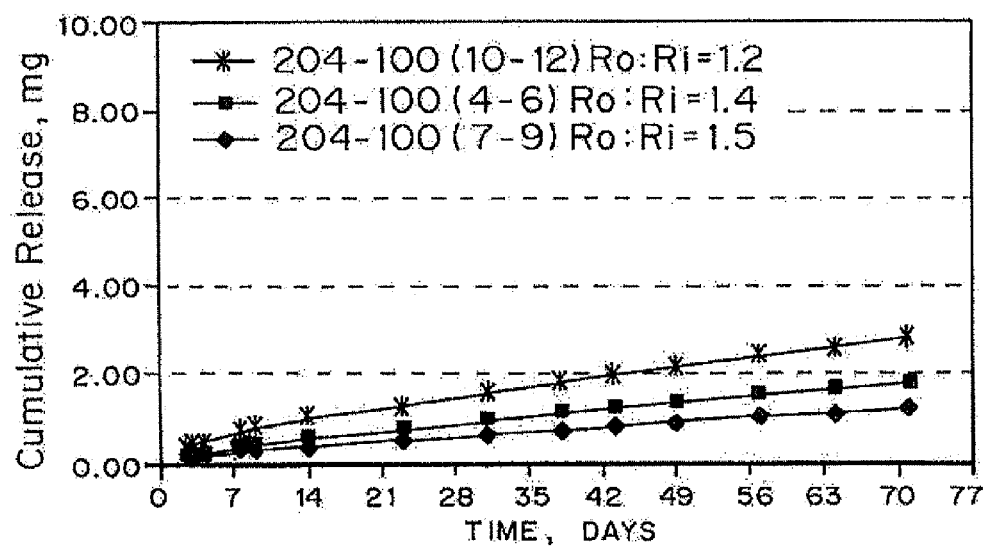
FIG. 11 shows the release of cromolyn sodium (mg) from coaxial implants with a hydrophobic PCL polymer membrane.

FIG. 11 shows the release of cromolyn from coaxial implants with a dense hydrophobic polymer membrane.

Example 7

Biodegradable Coaxial Implants for Delivery of a Protein

Using nitrogen gas as the core feed, a mixture comprising 30 vol % NaCl in PCL was extruded as described above through the outer ring of a coaxial die to form tubing having an overall diameter of about 3 mm. Implants containing α-interferon were prepared from the tubing by filling a short length of tubing with a suspension containing 20 mg of α-interferon in sucrose acetate isobutyrate (SAIB) and sealing the ends of the tube.

The implants, when incubated in phosphate buffered saline, released interferon for several days.

Modifications and variations of the coaxial implants and methods of manufacture and use thereof will be obvious to those skilled in the art from the foregoing detailed description. Such modifications and variations are intended to come within the scope of the following claims.

We claim:

1. A polymeric implant comprising a narcotic analgesic or a narcotic antagonist and a rate-controlling membrane, wherein the membrane is porous and has a pore volume ranging from about 5% to about 70%, wherein the implant comprises a rod, wherein the implant is a coaxial implant comprising a core containing the analgesic or antagonist and the rate controlling membrane, and wherein the analgesic or antagonist is released over a period of at least thirty days with zero order or near zero order release kinetics.

2. The implant of claim 1 wherein the analgesic or antagonist is selected from the group consisting of sufentanil, fentanyl, naltrexone, and naloxone.

3. The implant of claim 1 wherein the polymer is biodegradable.

4. The implant of claim 1 wherein the implant is a device selected from the group consisting of a matrix, prosthetic, graft, or coating.

5. The implant of claim 4 wherein the device is suitable for implantation intravascularly.

6. The implant of claim 5 wherein the device further comprises an active agent selected from the group consisting of heparin, taxol and other drugs for use in treating or preventing restenosis.

7. The implant of claim 4 suitable for implantation into a body lumen.

8. The implant of claim 4 suitable for implantation adjacent to a nerve plexus.

9. The implant of claim 1 wherein the core composition further comprises concentric layers having different compositions.

10. The implant of claim 1 wherein the core further comprises an excipient.

11. The implant of claim 1 wherein the rate-controlling membrane comprises pore forming agents.

12. The implant of claim 1 wherein the implant comprises a polymer selected from the group consisting of polyethylene glycol, polyhydroxyacid, caprolactone, or copolymer thereof.

13. The implant of claim 1 wherein the implant has sealed ends.

14. The implant of claim 1 wherein the implant is further processed by post-extrusion drawing or annealing.

15. A method of administering an analgesic or a narcotic antagonist thereof to a patient in need thereof comprising implanting the implant of claim 1 in the patient.

16. The implant of claim 1, wherein the rate-controlling membrane comprises pores ranging from about 1 micron to about 30 microns.

17. The implant of claim 1, wherein the rate controlling membrane comprises a polymer selected from the group consisting of polyhydroxyacids, polyanhydrides, polyorthoesters, polyetheresters, polyethylene glycol, polycaprolactone, polyesteramides, polyphosphazenes, polycarbonates, and copolymers and blends thereof.

* * * * *